United States Patent [19]

Cain et al.

[11] Patent Number: 5,366,957
[45] Date of Patent: Nov. 22, 1994

[54] HERBICIDAL 4-ACYL-5-ARYL ISOXAZOLE DERIVATIVES

[75] Inventors: Paul A. Cain; Susan M. Cramp, both of Ongar, England; Claude Lambert, Lyon, France

[73] Assignee: Rhone-Poulenc Argriculture Ltd, Essex, England

[21] Appl. No.: 913,914

[22] Filed: Jul. 17, 1992

[30] Foreign Application Priority Data

Jul. 17, 1991 [GB] United Kingdom ............ 9115377

[51] Int. Cl.$^5$ ............ A01N 43/80; C07D 261/08; C07D 261/12; C07D 261/14
[52] U.S. Cl. ............ 504/271; 548/248
[58] Field of Search ............ 548/248; 71/88; 504/271

[56] References Cited

U.S. PATENT DOCUMENTS 4,173,650 11/1979 Hanifin, Jr. et al. ............ 424/304
4,243,406 1/1981 Brannigan et al. ............ 71/88

FOREIGN PATENT DOCUMENTS

0418175A2 3/1991 European Pat. Off. .

OTHER PUBLICATIONS

Eiden et al., *Tetrahedron Letters*, No. 17, Apr. 1970, pp. 1439–1442.
*Chemical Abstracts*, vol. 105, No. 15, Oct. 13, 1986, abstract No. 133709w.
Smith et al, *J. Am. Chem. Soc.*, vol. 59, Jun. 1937, 1078–1082.

*Primary Examiner*—Marianne M. Cintins
*Assistant Examiner*—Phyllis Spivack
*Attorney, Agent, or Firm*—Burns, Doane, Swecker & Mathis

[57] ABSTRACT

5-Aryl isoxazole derivatives of formula (I):

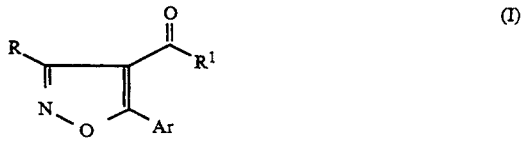

wherein:
Ar represents phenyl optionally substituted substituted by one or more groups $R^2$;
R represents hydrogen, $-CO_2R^3$, $-COR^4$, cyano, halogen, alkyl or haloalkyl;
$R^1$ represents alkyl, haloalkyl or cycloalkyl;
$R^2$ represents a halogen atom, $R^4$, nitro, $-CO_2R^3$, $-OR^4$, $-S(O)_mR^4$, $-S(O)_mR^5$, $-O-(CH_2)_p-OR^4$ or an alkyl group substituted by $-OR^4$;
$R^3$ and $R^4$, which may be the same or different, each represent alkyl or haloalkyl;
$R^5$ represents optionally substituted phenyl;
p represents an integer from 1 to 3; and
m represents zero, 1 or 2;
the herbicidal properties of these derivatives and their application to crop protection is described.

45 Claims, No Drawings

HERBICIDAL 4-ACYL-5-ARYL ISOXAZOLE DERIVATIVES

This invention relates to 5-aryl isoxazole derivatives, compositions containing them, processes for their preparation and their use as herbicides. U.S. Pat. No. 4,173,650 discloses 4-acetyl-5-(4'-fluorophenyl)isoxazole which is used as an intermediate in the preparation of compounds having anti-inflammatory activity. L. I. Smith et al (JACS, 1959, Vol. 59, 1078–1082) describes the preparation of a compound thought to be 4-acetyl-3-methyl-(2',3',4',5',6'-pentamethylphenyl) isoxazole. Neither of the above publications disclose any use of these compounds as herbicides. Belgian Patent No. 880,849 describes 5-aryl isoxazole compositions which may be used to prevent crop damage by herbicides.

The present invention provides 5-aryl isoxazoles of general formula I:

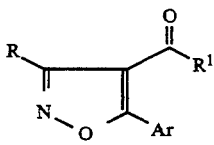

wherein:
Ar represents
  a phenyl group substituted by from one to five groups $R^2$; or
  a pyridyl group unsubstituted or substituted by from one to four groups $R^2$;
R represents:
  hydrogen, $-CO_2R^3$, $-COR^4$, cyano, halogen, or a straight- or branched-chain alkyl group containing up to 4 carbon atoms which is optionally substituted by one or more halogen atoms;
$R^1$ represents:
  a straight- or branched-chain alkyl group containing up to 6 carbon atoms which is optionally substituted by one or more halogen atoms or by a cycloalkyl group containing from 3 to 6 carbon atoms; or
  a cycloalkyl group containing from 3 to 6 carbon atoms optionally substituted by one or more groups $R^4$ or one or more halogen atoms;
$R^2$ represents:
  a halogen atom, $R^4$, nitro, $-CO_2R^3$, $-OR^4$, $-S(O)_mR^4$, $-S(O)_mR^5$, $-O-(CH_2)_p-OR^4$ or a straight- or branched-chain alkyl group containing up to 6 carbons which is substituted by $-OR^4$;
$R^3$ and $R^4$, which may be the same or different, each represent:
  a straight- or branched-chain alkyl group containing up to 6 carbon atoms which is optionally substituted by one or more halogen atoms;
$R^5$ represents a phenyl group optionally substituted by from one to five groups selected from halogen, nitro, $R^4$ and $-OR^4$;
p represents an integer from 1 to 3; and
m represents zero, 1 or 2;
with the proviso that
  (a) when R represents hydrogen and $R^1$ represents methyl, Ar is not 4-fluorophenyl; and
  (b) when R and $R^1$ both represent methyl, Ar is not 2,3,4,5,6-pentamethylphenyl;

which possess valuable herbicidal properties.

In certain cases the substituents R, $R^1$, $R^2$, $R^3$ and $R^4$ contribute to optical isomerism and/or stereoisomerism. All such forms are embraced by the present invention.

The compounds wherein R represents hydrogen, $R^1$ represents methyl and Ar represents 4-fluorophenyl; and wherein R and $R^1$ represent methyl and Ar represents 2,3,4,5,6-pentamethylphenyl are not considered per se as part of the invention but compositions containing them and their use as herbicides are considered part of the invention. A preferred class of compounds of formula (I), because of their herbicidal properties, are those wherein:
Ar represents:
  a phenyl group substituted by from one to five groups $R^2$; and
$R^2$ represents:
  a halogen atom, $R^4$, nitro, $-CO_2R^3$, $-OR^4$, $-S(O)_mR^4$, $-O-(CH_2)_p-OR^4$ or a straight- or branched- chain alkyl group containing up to 6 carbons which is substituted by $-OR^4$.

A further preferred class of compounds of formula (I) are those wherein:
  (a) R represents: a group selected from hydrogen, $CO_2R^3$ or $-COR^4$; and/or
  (b) Ar represents a phenyl group substituted by from one to three groups $R^2$.

A further preferred class of compounds of general formula (I) are those wherein:
Ar represents:
  phenyl group substituted by one or two groups $R^2$; or
  a pyridyl group substituted by a group $S(O)_mR^4$;
R represents hydrogen or $-CO_2R^3$;
$R^1$ represents cyclopropyl;
$R^2$ represents a group selected from halogen, $R^4$, $-S(O)_mR^4$ and $-S(O)_mR^5$.

Particularly important compounds because of their herbicidal properties include the following:
1.  4-cyclopropylcarbonyl-5-(2-fluoro-4-methylsulphonylphenyl)isoxazole;
2.  4-cyclopropylcarbonyl-5-(3,4-dichlorophenyl)isoxazole;
3.  4-cyclopropylcarbonyl-5-[4-(methylsulphenyl)-phenyl]isoxazole;
4.  4-cyclopropylcarbonyl-5-[3-chloro-4-(methylsulphenyl)phenyl]isoxazole;
5.  4-cyclopropylcarbonyl-5-[3-chloro-4-(methylsulphonyl)phenyl]isoxazole;
6.  4-cyclopropylcarbonyl-5-[4-(methylsulphonyl)-phenyl]isoxazole;
7.  4-cyclopropylcarbonyl-5-[4-(methylsulphinyl)-phenyl]isoxazole;
8.  4-cyclopropylcarbonyl-5-[3-(methylsulphenyl)-phenyl]isoxazole;
9.  ethyl 5-[2-chloro-4-(methylsulphenyl)phenyl]-4-cyclopropylcarbonylisoxazole-3-carboxylate;
10. ethyl 4-cyclopropylcarbonyl-5-[2-(methylsulphenyl)-4-trifluoromethylphenyl]isozole-3-carboxylate;
11. 1-methylethyl 4-cyclopropylcarbonyl-5-[2-(methylsulphenyl)-4trifluoromethylphenyl]isoxazole-3-carboxylate;
12. 4-cyclopropylcarbonyl-5-[2-(phenylsulphenyl)-4trifluoromethylphenyl]isoxazole; and
13. 4-cyclopropylcarbonyl-5-[5-(methylsulphenyl)pyrid-2-yl]isoxazole.

The numbers 1 to 13 are assigned to the above compounds for identification and reference hereinafter.

By the processes described hereinafter the following compounds of general formula (I) may also be prepared and are also of interest:

| R | R¹ | Ar is a phenyl group substituted as follows | | |
|---|---|---|---|---|
| | | 2-position | 3-position | 4-position |
| H | Cyclopropyl | Br | H | S(O)Me |
| CO₂Et | Cyclopropyl | CF₃ | H | S(O)Et |
| H | Me | CF₃ | H | SO₂Me |
| H | Cyclopropyl | CF₃ | H | Cl |
| H | Cyclopropyl | NO₂ | H | Cl |
| H | Isopropyl | Cl | H | SO₂Me |
| H | Cyclopropyl | F | H | CF₃ |
| H | Isopropyl | F | H | SO₂Me |
| CO₂Et | 1-Me-cyclopropyl | H | S(O)Et | Br |
| CO₂Et | 1-Me-cyclopropyl | H | H | SO₂Et |
| CO₂Et | 1-Me-cyclopropyl | H | OCH₂CH₂OMe | SO₂Me |
| CO₂Me | Cyclopropyl | H | SO₂Me | H |
| CO₂Me | Isopropyl | H | SMe | CF₃ |
| CO₂Me | Isopropyl | H | S(O)Me | CF₃ |
| CO₂Et | Cyclopropyl | Me | H | S(O)Me |
| H | Cyclopropyl | Me | H | S(O)Me |
| H | 1-Me-cyclopropyl | NO₂ | H | CF3 |
| CO₂Et | Cyclopropyl | NO₂ | H | Cl |
| H | Cyclopropyl | NO₂ | H | SMe |
| H | Me | NO₂ | H | CF₃ |
| H | Cyclopropyl | SMe | —OCH₂CH₂OMe | Cl |
| H | Cyclopropyl | SMe | H | H |
| H | Cyclopropyl | SMe | H | OMe |
| CO₂Me | Cyclopropyl | SMe | H | SMe |
| CO₂Me | Me | SO₂Me | Br | Br |
| CO₂Me | 1-Me-cyclopropyl | SO₂Me | H | H |
| H | Cyclopropyl | SO₂Me | H | Br |
| H | Cyclopropyl | SO₂Me | H | CF₃ |
| CO₂Et | Cyclopropyl | SO₂Me | H | Cl |
| CO₂Et | Cyclopropyl | SO₂Me | Cl | Cl |
| CO₂Et | Cyclopropyl | SO₂Me | H | Cl |
| H | Cyclopropyl | SO₂Me | H | Cl |
| H | Cyclopropyl | SO₂Me | OMe | Cl |
| H | Cyclopropyl | SO₂Me | H | Me |
| H | Cyclopropyl | S(O)Et | H | F |
| H | Cyclopropyl | S(O)Me | Cl | Cl |
| CO₂Et | Cyclopropyl | S(O)Me | H | CF₃ |
| H | Cyclopropyl | H | SMe | Cl |
| CO₂Et | Cyclopropyl | CF₃ | H | SO₂Me |
| H | Cyclopropyl | CF₃ | H | SO₂Me |
| H | Cyclopropyl | Cl | OMe | SO₂Me |
| CO₂Me | Cyclopropyl | Cl | OMe | SO₂Me |
| H | Cyclopropyl | SO₂Me | Cl | Cl |
| H | Cyclopropyl | CH₃ | CO₂Me | SO₂Me |
| CO₂Me | Cyclopropyl | CH₃ | CO₂Me | SO₂Me |
| H | Cyclopropyl | Cl | H | SO₂Me |
| H | Cyclopropyl | OMe | H | SO₂Me |
| H | Cyclopropyl | Br | OMe | S(O)Me |

Compounds of general formula (I) may be prepared by the application or adaptation of known methods (i.e. methods heretofore used or described in the literature), for example methods as hereinafter described. In the following description where symbols appearing in formulae are not specifically defined, it is to be understood that they are "as hereinbefore defined" in accordance with the first definition of each symbol in this specification. According to a feature of the present invention compounds of general formula (I) may be prepared by the metallation of compounds of general formula (II):

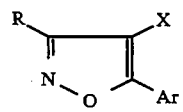

(II)

wherein X is a halogen atom, followed by reaction of the compound thus obtained with an acid chloride of general formula R¹COCl. Generally X is bromine or iodine and the reaction performed with for example n-butyllithium in an inert solvent such as ether or tetrahydrofuran at a temperature from −78° C. to 0° C.

According to a further feature of the present invention compounds of general formula (I) may be prepared by the oxidation of compounds of general formula (III):

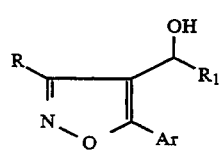

(III)

to convert the hydroxy group to a ketone group. The reaction is generally performed for example using a mixture prepared from chromium trioxide and aqueous sulphuric acid.

According to a further feature of the present invention compounds of general formula (I) may be prepared by the reaction of compounds of general formula (IV):

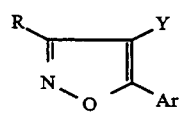

(IV)

in which Y represents a carboxy group, or a reactive derivative thereof (such as a carboxylic acid chloride or carboxylic ester), or a cyano group, with an appropriate organometallic reagent such as a Grignard reagent or an organolithium reagent, to introduce a group —COR¹. The reaction is generally carried out in an inert solvent such as ether or tetrahydrofuran, at a temperature from 0° C. to the reflux temperature of the solvent.

According to a further feature of the present invention compounds of general formula (I) in which R is a hydrogen atom may be prepared by the reaction of compounds of general formula (V):

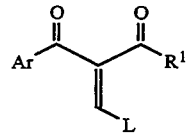

(V)

wherein L is a leaving group such as O-alkyl or N,N-dialkyl with a salt of hydroxylamine. Hydroxylamine hydrochloride is generally preferred. The reaction is generally carried out in a solvent such as ethanol or acetonitrile, optionally in the presence of a base or acid acceptor such as triethylamine or sodium acetate.

According to a further feature of the present invention compounds of general formula (I) in which R is not a hydrogen atom may be prepared by the reaction of a compound of general formula (VI):

wherein P is a leaving group such as N,N-dialkyl or —S-alkyl, with a compound of general formula RC(X)=N—OH wherein X is as hereinbefore defined and R is not hydrogen. Generally X is chlorine or bromine. The reaction is generally performed in an inert solvent such as toluene or dichloromethane either in the presence of a base such as triethylamine or a catalyst such as a 4A molecular sieve or fluoride ion.

According to a further feature of the present invention compounds of general formula (I) in which R is not hydrogen may be prepared by the reaction of compounds of general formula (VII):

with a compound of general formula RC(X)=N—OH, wherein X is as hereinbefore defined and R is not hydrogen. Generally X is chlorine or bromine. The reaction is generally performed in an inert solvent such as toluene or dichloromethane, optionally in the presence of a base such as triethylamine, or a catalyst such as a 4A molecular sieve or fluoride ion.

According to a further feature of the present invention compounds of general formula (I) in which R is not hydrogen may be prepared by the reaction of a salt of compounds of general formula (VIII):

with a compound of general formula RC(X)=NOH wherein X is as hereinbefore defined and R is not hydrogen. Generally X is chlorine or bromine. Preferred salts include the sodium and magnesium salts.

Intermediates used in the preparation of compounds of general formula (I) may be prepared by the application or adaptation of known methods for example methods described hereinafter.

Compounds of general formula (III) may be prepared by metallation of compounds of general formula (II) with for example n-butyllithium in an inert solvent such as ether or tetrahydrofuran at a temperature from −78° C. to 0° C., followed by reaction with an aldehyde of general formula $R^1CHO$.

Compounds of general formula (IV) in which R is a hydrogen atom and Y is —$CO_2$-alkyl or —CN may be prepared by the reaction of compounds of general formula (IX):

wherein $Y^1$ represents —$CO_2$-alkyl or —CN and L is as hereinbefore defined, with a salt of hydroxylamine such as hydroxylamine hydrochloride, in a solvent such as ethanol or acetonitrile, optionally in the presence of a base or acid acceptor such as triethylamine or sodium acetate.

Compounds of general formula (IV) in which Y represents a carboxylic acid or carboxylic acid chloride may be prepared from the corresponding compound of general formula (IV) in which Y represents a carboxylic ester group by the hydrolysis of said ester group and conversion, as necessary, of the acid thus obtained to the acid chloride, e.g. by heating with thionyl chloride.

Compounds of general formula (IX) may be prepared by the reaction of a ketoester or ketonitrile of general formula (X):

wherein $y^1$ is as hereinbefore defined with either a trialkyl orthoformate (e.g. triethyl orthoformate) in the presence of acetic anhydride at the reflux temperature of the mixture, or with a dialkylformamide dialkylacetal (e.g. dimethylformamide dimethylacetal) optionally in an inert solvent such as toluene at a temperature from room temperature to the reflux temperature of the mixture.

Compounds of general formula (IV) in which R is not hydrogen may be prepared by the reaction of compounds of general formula (X) with a compound of general formula RC(X)=NOH wherein X is as hereinbefore defined and R is not hydrogen. Generally X is chlorine or bromine.

Compounds of general formula (V) may be prepared by the reaction of compounds of general formula (VIII) with either a trialkyl orthoformate (e.g. triethyl orthoformate) in the presence of acetic anhydride at the reflux temperature of the mixture, or with a dialkylformamide dialkylacetal (e.g. dimethylformamide dimethylacetal) optionally in an inert solvent such as toluene at a temperature from room temperature to the reflux temperature of the mixture.

Compounds of general formula (VI) may be prepared by the reaction of a compound of general formula (XI):

wherein P is as hereinbefore defined with an acid chloride of general formula $R^1COCl$ in an inert solvent such as dichloromethane or toluene, in the presence of a base such as triethylamine.

Compounds of general formula (VII) may be prepared by the metallation of the appropriate acetylene of general formula (XII):

wherein $X^1$ represents hydrogen or halogen (e.g. bromine), using for example n-butyllithium in an inert solvent such as ether or tetrahydrofuran at a temperature from −78° C. to 0° C., followed by treatment with an acid chloride of general formula $R^1COCl$.

Compounds of general formula (II) may be prepared by the halogenation of compounds of general formula (XIII):

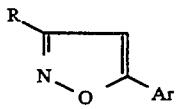

for example by heating with bromine or iodine in the presence of concentrated nitric acid.

Compounds of general formula (XIII) may be prepared by the reaction compounds of general formula (XIV):

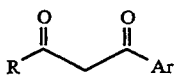

with a salt of hydroxylamine such as hydroxylamine hydrochloride, in a solvent such as ethanol or acetonitrile, optionally in the presence of a base or acid acceptor such as triethylamine or sodium acetate.

Compounds of general formula (VIII), (IX), (X), (XI), (XII) and (XIV) may be prepared by the application or adaptation of known methods.

Those skilled in the art will appreciate that some compounds of general formula (I) may be prepared by the interconversion of other compounds of general formula (I) and such interconversions constitute yet further features of the present invention. Examples of such interconversions are hereafter described.

Compounds in which R represents a cyano group may be prepared from compounds in which R represents an ester group —$CO_2R^3$ wherein $R^3$ is as hereinbefore defined via hydrolysis to the corresponding carboxylic acid, conversion to the corresponding acid chloride by reaction with for example thionyl chloride, treatment with ammonia to give the amide and dehydration with for example phosphorus oxychloride.

Compounds in which $R^2$ represents a group —$SOR^4$ or —$SO_2R^4$ may be prepared by the oxidation of compounds in which $R^2$ represents a group —$SR^4$ using for example 3-chloroperbenzoic acid in an inert solvent such as dichloromethane at a temperature from −40° C. to 0° C.

The following examples illustrate the preparation of compounds of general formula (I). In the present specification b.p. means boiling point, m.p. means melting point. Where the letters NMR appear, the characteristics of the proton nuclear magnetic resonance spectrum follow. Unless otherwise specified the percentages are by weight.

EXAMPLE 1

Sodium acetate (7.4g) was added to a mixture of hydroxylamine hydrochloride (6.3 g) and 3-cyclopropyl-2-ethoxymethylene-1-(2-fluoro-4-methylsulphonylphenyl)-propan-1,3-dione (29.0g) in ethanol. The mixture was stirred at room temperature overnight. The solvent was evaporated and the residue was partitioned between ethyl acetate and water. The organic phase was washed with water, dried (anhydrous magnesium sulphate) filtered and evaporated to dryness. The residue was triturated with ether and filtered. The resultant solid was recrystallized from methanol. The mother liquors from the recrystallization were combined and evaporated to dryness. The residue was purified by column chromatography on silica gel to give 4-cyclopropylcarbonyl-5-(2-fluoro-4-methylsulphonylphenyl)-isoxazole (compound 1) as a white solid, m.p. 129.5°–130.5° C.

By proceeding in a similar manner the following compounds were prepared from the appropriately substituted starting materials:

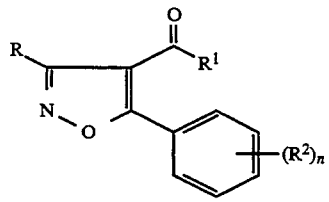

| Comp No. | R | $R^1$ | $(R^2)_n$ | m.p./NMR |
|---|---|---|---|---|
| 2 | H | Cp | 3,4-$Cl_2$ | NMR:($CDCl_3$) 1.1(m, 2H) 1.35 (m, 2H) 2.3(m, 1H) 7.6(d, 1H) 7.95(d, 1H) 8.25(s, 1H) 8.75(s, 1H) |
| 3 | H | Cp | 4-SMe | m.p: 94–86° C. |
| 4 | H | Cp | 3-Cl-4-SMe | m.p: 96–87.5° C. |
| 8 | H | Cp | 3-SMe | NMR: ($CDCl_3$) 1.0(m, 2H) 1.4(m, 2H) 2.25(m, 1H) 2.55(s, 3H) 7.4(d, 2H) 7.7(m, 1H) 7.9(s, 1H) 8.7(s, 1H) |
| 12 | H | Cp | 2-SPh-4-$CF_3$ | NMR: ($CDCl_3$) 0.85(m, 2H) 1.15(m, 2H) 1.9(m, 1H) 7.25(s, 5H) 7.4(s, 1H) 7.5(m, 2H) 8.6(s, 1H) |

Note: Cp represents cyclopropyl

EXAMPLE 2

A mixture of 1-[2-chloro-4-(methylsulphenyl)-phenyl]-3-cyclopropylprop-1-yn-3-one (1.39g) and ethyl chloro-oximidoacetate (0.84 g) in toluene was stirred and heated at reflux overnight. It was cooled and evaporated to dryness. The residue was purified by chromatography eluted with a mixture of hexane and dichloromethane, followed by ether to give ethyl 5-[2-chloro-4(methylsulphenyl)phenyl]-4-cyclopropylcarbonylisoxazole-3-carboxylate (compound 9, 0.72g) as an orange solid, m.p. 50° C.

By proceeding in a similar manner the following compounds were prepared from the appropriately substituted starting materials:

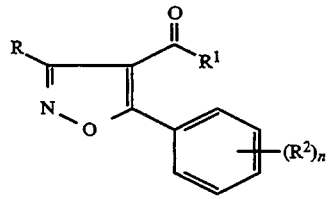

| Comp No. | R | $R^1$ | $(R^2)_n$ | m.p. |
|---|---|---|---|---|
| 10 | $CO_2Et$ | Cp | 2-SMe-4-$CF_3$ | 98–100° C. |
| 11 | $CO_2iPr$ | Cp | 2-SMe-4-$CF_3$ | 104–105° C. |

Note: Cp represents cyclopropyl

EXAMPLE 3

A mixture of 5-[3-chloro4-(methylsulphenyl)-phenyl]4-cyclopropylcarbonyl-isoxazole (1.0 g) and 3-chloroperoxybenzoic acid (2.3g, 50%) in dichloromethane was stirred overnight. A saturated solution of sodium bisulphite was added and the layers were separated. The organic phase was washed with sodium bicarbonate solution, water, dried (MgSO$_4$) and filtered. The filtrate was evaporated to dryness to give 4-cyclopropylcarbonyl-5-[3-chloro-4-(methylsulphonyl)-phenyl]isoxazole (compound 5, 1.11 g) as a white solid, m.p. 148°–150° C.

By proceeding in a similar manner the following compounds were prepared from the appropriately substituted starting materials.

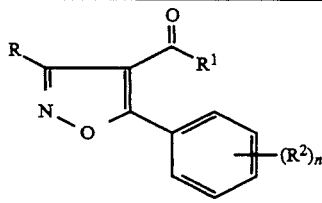

| Compound No. | R | R$^1$ | (R$^2$)$_n$ | m.p. |
| --- | --- | --- | --- | --- |
| 6 | H | Cp | 4-SO$_2$Me | 102–104° C. |
| 7 | H | Cp | 4-SOMe | 97–99° C. |

Note: Cp represents cyclopropyl

EXAMPLE 4

Sodium acetate (1.1 g) was added to a solution of hydroxylamine hydrochloride (0.9 g) and 3-cyclopropyl-2-(N,N-dimethylaminomethylene )- 1-[5-(methylsulphenyl)-pyrid-2-yl]propan-1,3-dione (3.24 g) in ethanol. The mixture was stirred for 1 hour then cooled and filtered. The solid was washed with cold ethanol and the filtrate was partially evaporated. Water was added and the mixture was stirred at 0° C. for 0.5 hours. It was extracted with dichloromethane washed with water, dried (Na$_2$SO$_4$) and filtered. The filtrate was evaporated to dryness and the residue was purified by chromatography eluted with mixture of ethyl acetate and hexane to give 4-cyclopropylcarbonyl-5-[5-(methylsulphenyl)pyrid-2-yl]isoxazole (compound 13, 0.41 g) as a white solid, m.p. 103°–104° C.

REFERENCE EXAMPLE 1

A mixture of 3-cyclopropyl-1-(2-fluoro-4-methylsulphonylphenyl)-propan-1,3-dione (7.4 g), triethyl orthoformate (8.5 g) and acetic anhydride was stirred and heated at reflux for 4 hours. The mixture was evaporated to dryness. Xylene was added and the mixture was re-evaporated to give 3-cyclopropyl-2-ethoxymethylene-1-(2-fluoro-4-methylsulphonylphenyl)-propan-1,3-dione (8.8 g) as a red oil which was not further purified.

By proceeding in a similar manner, the following compounds were prepared from the appropriately substituted starting materials.

| R$^1$ | (R$^2$)$_n$ |
| --- | --- |
| Cyclopropyl | 3,4-Cl$_2$ |
| Cyclopropyl | 4-SMe |
| Cyclopropyl | 3-Cl-4-SMe |
| Cyclopropyl | 3-SMe |
| Cyclopropyl | 2-SPh-4-CF$_3$ |

A mixture of t-butyl 3-cyclopropyl-2-(2-fluoro-4-methylsulphonylbenzoyl)-3-oxopropionate (10.5 g) and p-toluenesulphonic acid (2.0 g) in toluene was stirred and heated at reflux for 4 hours. The mixture was washed with water, dried (anhydrous magnesium sulphate) and filtered. The filtrate was evaporated to dryness to give 3-cyclopropyl-1-(2-fluoro-4-methylsulphonylphenyl)-propan-1,3-dione (7.4 g) as a red gum, NMR (CDCl$_3$); 0.9–1.3 (m,4H), 1.8–2.1 (m, 1H), 3.1 (s,3H), 6.3 (s, 1H), 7.5–8.0 (m,3H).

By proceeding in a similar manner 3-cyclopropyl-1-(3,4-dichlorophenyl)-propan-1,3-dione was prepared from the appropriately substituted starting material.

REFERENCE EXAMPLE 3

A mixture of magnesium (0.7g) and t-butyl 3-cyclopropyl-3-oxopropionate (4.97g) in methanol was stirred and carbon tetrachloride (1 ml) was added. The mixture was stirred for 1 hour and evaporated to dryness. Toluene was added and the mixture was re-evaporated to dryness. The residue was dissolved in acetonitrile and 2-fluoro4-methylsulphonylbenzoyl chloride (6.5 g) was added. The mixture was stirred for 4 hours, evaporated to dryness and dissolved in ethyl acetate, washed with dilute hydrochloric acid, dried (anhydrous magnesium sulphate) and filtered. The filtrate was evaporated to dryness to give t-butyl 3-cyclopropyl-(2-fluoro4-methylsulphonylbenzoyl)-3-oxopropionate (10.5 g) as a red gum which was not purified further.

By proceeding in a similar manner (replacing acetonitrile by toluene as the reaction solvent) 3-cyclopropyl-(3,4-dichlorobenzoyl)-3-oxopropionate was prepared from the appropriately substituted starting material:

REFERENCE EXAMPLE 4

A mixture of 2-fluoro-4-methylsulphonylbenzoic acid (6.0 g) and thionyl chloride were stirred and heated at reflux for 2 hours. The mixture was cooled and evaporated to dryness. Toluene was added and the solvent re-evaporated to 1.5 give 2-fluoro4-methylsulphonylbenzoyl chloride (6.5 g) as a brown solid which was not further purified.

REFERENCE EXAMPLE 5

2-Fluoro4-(methylsulphenyl)-toluene (25.4 g) was suspended in water and the suspension warmed to 100° C. Potassium permanganate (119.2 g) was added at such a rate as to maintain the temperature around 100° C. The resulting suspension was filtered and the solid washed with hot water. The cooled filtrate was extracted with ethyl acetate. The aqueous layer was acidified to pH 1 and extracted with ethyl acetate. The organic phase was dried (anhydrous magnesium sulphate) and filtered. The filtrate was evaporated to dryness to give 2-fluoro-4-methylsulphonylbenzoic acid (15.9 g) as an orange solid, m.p. 187°–188° C. REFERENCE EXAMPLE 6

A mixture of 3-fluoro-4-methylaniline (25 g), dimethyl disulphide (375 g) and t-butyl nitrite (30 ml) in 1,2-dichloroethane was warmed to start the reaction. A solution of 3-fluoro-4-methylaniline (225 g) in 1,2-dichloroethane was added dropwise, simultaneously with t-butyl nitrite (241 ml) at such a rate as to maintain the temperature below 60° C. The mixture was stirred for 2 hours, then water was added. The organic layer was washed with water, hydrochloric acid, dried (anhydrous magnesium sulphate) and filtered. The filtrate was evaporated to dryness and the residue was distilled to give 2-fluoro-4-(methylsulphenyl)toluene (164 g) as a yellow oil; NMR (acetone-d6); 2.2 (3H,d), 2.5 (3H,s), 7.05 (3H,m).

REFERENCE EXAMPLE 7

A mixture of 3-cyclopropyl- 1-[5-(methylsulphenyl )-pyrid-2-yl]propan- 1,3-dione (2.9 g), dimethylformamide dimethyl acetate and dioxane was stirred at room temperature overnight. It was evaporated to dryness and the residue was triturated with ether and filtered to give 3-cyclopropyl-2-(N,N-dimethylaminomethylene)-1-[5-(methylsulphenyl)-pyrid-2-yl]propan- 1,3-dione (3.24 g) as a brown solid which was used without further characterization.

REFERENCE EXAMPLE 8

Cyclopropyl methyl ketone (0.84 g) was added to a suspension of sodium hydride (80%, 0.3 g) in dioxane. The mixture was stirred for 20 minutes and ethyl 4(methylsulphenyl)benzoate (1.0 g) was added. The mixture was stirred and heated at 45° C. for 1.5 hours and at 60° C. for 2 hours. It was left to stand at room temperature overnight. Hydrochloric acid (2M) was added and the mixture was extracted with ethyl acetate, washed with water, dried (MgSO4) and filtered. The filtrate was evaporated to dryness and the residue was purified by chromatography eluted with a mixture of ethyl acetate and hexane to give 3-cyclopropyl-1-[4-(methylsulphenyl)-phenyl]-propan-1,3-dione (0.59 g) as an orange solid, NMR (CDCl3) 1.0(m,2H), 1.2(m,2H), 1.8(m, 1H), 2.5(s,3H), 6.25(s, 1H), 7.25(d,2H), 7.8(d,2H), 16.35(bs, 1H).

By proceeding in a similar manner the following compounds were prepared from the appropriately substituted starting materials using the solvent described, to carry out the reaction.

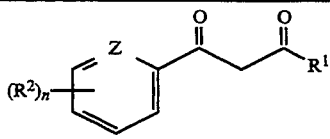

| R¹ | Z | (R²)$_n$ | Solvent | NMR/m.p. |
| --- | --- | --- | --- | --- |
| Cyclopropyl | CH | 3-Cl-4-SMe | Ether | 102–105° C. |
| Cyclopropyl | CH | 3-SMe | THF | 1 |
| Cyclopropyl | CH | 2-SPh-4-CF3 | THF | 2 |
| Cyclopropyl | N | 5-SMe | Ether | 85–87° C. |

Note:
1. NMR(CDCl3): 0.8–1.5(m, 4H), 1.7–2.1(m, 1H), 2.55(s, 3H), 6.25(s, 1H), 7.2–7.85(m, 4H).
2. NMR(CDCl3): 0.95(m, 2H), 1.2(m, 2H), 1.7(m, 1H), 6.05(s, 1H), 7.15(s, 1H) 7.3–7.5(m, 6H), 7.6(d, 1H).

REFERENCE EXAMPLE 9

A solution of 2-(phenylsulphenyl)-4-trifluoromethylbenzoic acid ( 11.5 g) and thionyl chloride ( 11.4 g) in dichloroethane containing a few drops of DMF was heated at reflux for 1.5 hours. The mixture was evaporated to dryness and methanol was added. The mixture was heated at reflux for 1 hour and evaporated to dryness. It was treated with water and extracted with ether, washed with sodium carbonate solution (2M), water, dried (Na2SO4) and filtered. The filtrate was evaporated to dryness and the residue was triturated with cyclohexane and filtered to give methyl 2-(phenylsulphenyl)-4-trifluoromethylbenzoate (10.5 g) as a white solid, m.p. 55°–60° C.

REFERENCE EXAMPLE 10

A mixture of 2-(phenylsulphenyl)4-trifluoromethylbenzonitrile (90 g) in sulphuric acid (50%) was stirred and heated at reflux for 10 hours. After cooling it was diluted with water and extracted with dichloromethane. The organic layer was extracted with aqueous sodium hydroxide (2M) and the aqueous phase was acidified to pH 1, extracted with dichloromethane, dried (Na2SO4) and filtered. The filtrate was evaporated to dryness to give 2-(phenylsulphenyl)-4trifluomethylbenzoic acid (75 g) as yellow solid, m.p. 161°–164° C.

REFERENCE EXAMPLE 11

A mixture of 2-nitro4-trifluoromethylbenzonitrile (8.64 g), thiophenol (4.4 g) and potassium carbonate (6.9 g) in acetonitrile was stirred at room temperature for 1 hour then heated at reflux for 9 hours. Thiophenol (0.3 ml) was added and the mixture was stirred and heated at reflux for 1 hour. Water was added and the mixture was extracted with dichloromethane, dried (MgSO4) and filtered. The filtrate was evaporated to dryness and the residue was recrystallized from n-hexane to give 2-(phenylsulphenyl)-4-trifluoromethylbenzonitrile (9.5 g) as a white solid, m.p. 51° C.

REFERENCE EXAMPLE 12

A solution of n-butyllithium in hexane (4.4 ml) was added to a stirred solution of [2-chloro-4-(methylsulphenyl)phenyl]acetylene (2.0 g) in THF while maintaining the temperature below −70° C. The mixture was stirred for 5 minutes and cyclopropanecarbonyl chloride (2.4 g) was added. The mixture was warmed to room temperature and poured onto aqueous sodium chloride solution. The aqueous layer was extracted with ether and combined organic layers dried (MgSO4) and filtered. The filtrate was evaporated to dryness and the residue was dissolved in methanol and heated at reflux for 5 minutes. Toluene was added and the mixture was evaporated to dryness. The residue was purified by chromatography eluted with a mixture of hexane and ether to give 1-[2-chloro4(methylsulphenyl)phenyl]-3-cyclopropylprop-1-yn-3-one as yellow oil which crystallized on standing, m.p. 46°–50° C. [2-Chloro-4-(methylsulphenyl)phenyl]acetylene was prepared by the reaction of 1-bromo-2-[2-chloro-4-(methylsulphenyl)-phenyl]acetylene with n-butyllithium and wet zinc chloride in THF at −70° C.

REFERENCE EXAMPLE 13 n-Butyllithium (2.5M, 1.45 ml) was added to a stirred cooled solution of 1-bromo-2-[2-(methylsulphenyl)4-trifluoromethylphenyl]acetylene and 1,1-dibromo-2-[2-(methylsulphenyl)4-trifluoromethylphenyl]ethene (1.0 g) in THF, maintaining the temperature below −70°C. The mixture was stirred for 30 minutes and cyclopropanecarbonyl chloride (0.75 g) was added. The temperature was allowed to rise to room temperature and the mixture was stirred for 2 hours, aqueous ammonium chloride was added and the mixture was extracted with ether, dried (MgSO4) and filtered. The filtrate was evaporated to dryness and the residue was purified by chromotography eluted with a mixture of hexane and ether to give 3-cyclopropyl-1-[2-(methylsulphenyl )-4-trifluoromethylphenyl]prop- 1-yn-3one (0.64 g) as yellow oil, NMR (CDCl3) 1.15(m,2H), 1.45(m,2H), 2.2(m,1H), 2.6(s,1H), 7.35(d,1H) 7.4(s,1H), 7.6(d, 1H).

REFERENCE EXAMPLE 14

A suspension of Triton B (Reg Trade Mark, N-benzyltrimethylammonium hydroxide, 40% in methanol, 1.8 g) in toluene was added to a solution of 1,1-dibromo-2-[2-chloro-4-(methylsulphenyl)phenyl]ethene (0.96 g) in toluene. The mixture was stirred for 15 minutes. Sulphuric acid (2 m) was added and the resulting layers were separated. The organic layer was washed with water, dried (MgSO$_4$) and filtered. The filtrate was evaporated to dryness and the residue was purified by chromotography eluted with a mixture of hexane and dichloromethane to give 1-bromo-2-[2-chloro-4-(methylsulphenyl)phenyl]acetylene 90.78 g) as a yellow oil, NMR (CDCl$_3$) 2.5 (s,3H), 7.05(d,1H), 7.2(s,1H), 7.35(d,1H).

By proceeding in a similar manner the following compound was prepared from the appropriately substituted starting material.

1-Bromo-2-[2-(methylsulphenyl)-4-trifluoromethylphenyl]acetylene as a mixture containing unreacted 1,1-dibromo-2-[methylsulphenyl-4trifluoromethylphenyl]ethene.

REFERENCE EXAMPLE 15

Triphenyl phosphine (2.5 g) was added to a stirred solution of carbon tetrabromide (1.48 g) in dichloromethane maintaining the temperature at 0° C. The mixture was stirred for 0.5 hours and 2-chloro-4-(sulphenyl)-benzaldehyde (1.0 g) was added. The resultant mixture was stirred for 0.5 hours and poured into hexane. The resulting solid was filtered off and washed with ether. The combined filtrates were evaporated to dryness and the residue was purified by chromatrography eluted with hexane to give 1,1-dibromo-2-[2-chloro-4-(methylsulphenyl)phenyl]ethene (0.96 g) as a white solid, NMR (CDCl$_3$) 2.45 (s,3H), 7.15(d,1H), 7.25(s,1H), 7.55(s,1H), 7.6(d,1H).

By proceeding in a similar manner the following compound was prepared from the appropriately substituted starting material.

1,1-Dibromo-2-[2-(methylsulphenyl)-4-trifluoromethylphenyl]ethene as a white solid, NMR (CDCl$_3$) 2.5 (s,3H), 7.4–7.7(m,4H).

REFERENCE EXAMPLE 16

A mixture of 2-chloro-4-(methylsulphenyl)-benzoyl chloride ( 1.0 g), triphenyl phosphine (2.47 g) and bis(-triphenylphosphine)copper (I) borohydride (1.0 g) in acetone was stirred at 0° C. for 1 hour. Further bis (triphenylphosphine)copper (I) borohydride (1.5 g) was added and the mixture was stirred for 2 hours. The mixture was filtered and the filtrate was evaporated to dryness. The residue was dissolved in chloroform and treated with copper (I) bromide (2.1 g). The filtrate was evaporated to dryness and the residue was purified by chromotography eluted with a mixture of ethyl acetate and hexane to give 2-chloro-4-(methylsulphenyl)benzaldehyde (0.83 g) as an off-white solid, m.p. 76°–77° C.

By proceeding in a similar manner 2-(methylsulphenyl)-4-trifluoromethylbenzaldehyde was prepared from the appropriately substituted starting material.

REFERENCE EXAMPLE 17 n-Butyllithium (2.5M in hexane, 25 ml) was added under an inert atmosphere to a stirred solution of 4-bromo-3-(methylsulphenyl)benzotrifluoride (16.4 g) in ether maintaining the temperature below −70° C. for 2 hours. The mixture was poured onto solid carbon dioxide pellets, stirred for 10 mins and aqueous hydrochloric acid added. The layers were separated and the aqueous layer was extracted with ether. The combined organic layers were washed with water, dried (MgSO$_4$) and filtered. The filtrate was evaporated and the residue was triturated with cyclohexane and filtered to give 2-(methylsulphenyl)-4-trifluoromethylbenzoic acid (12.4 g) as a white solid NMR (CDCl$_3$+DMSO-d$_6$): 2.45 (s,3H), 7.2(d,1H), 7.3(s,1, H), 8.0(d,1H), 10.7–11 (bs,1H).

REFERENCE EXAMPLE 18 t-Butyl nitrite (3 ml) was added to a mixture of 3-amino-4-bromobenzotrifluoride (4 g) and dimethyl disulphide (15 ml) in chloroform. The mixture was warmed until reaction started when t-butyl nitrite ( 11 ml) and a solution of 3-amino-4-bromobenzotrifluoride (16 g) in chloroform were added simultaneously. The resultant mixture was stirred for 24 hours, washed with water, hydrochloric acid (2M), water, dried (MgSO$_4$) and filtered. The filtrate was evaporated to dryness and the residue was distilled to give 4-bromo-3-(methylsulphenyl)benzotrifluoride (16.4 g) as a yellow oil, b.p. 84°–88° C. at 2 mm Hg.

According to a feature of the present invention, there is provided a method for controlling the growth of weeds (i.e. undesired vegetation) at a locus which comprises applying to the locus a herbicidally effective amount of at least one 5-aryl isoxazole derivative of general formula (I). For this purpose, the 5-aryl isoxazole derivatives are normally used in the form of herbicidal compositions (i.e. in association with compatible diluents or carriers and/or surface active agents suitable for use in herbicidal compositions), for example as hereinafter described.

The compounds of general formula (I) show herbicidal activity against dicotyledonous (i.e. broad-leafed) and monocotyledonous (i.e. grass) weeds by pre- and-/or post-emergence application.

By the term "pre-emergence application" is meant application to the soil in which the weed seeds or seedlings are present before emergence of the weeds above the surface of the soil. By the term "post-emergence application" is meant application to the aerial or exposed portions of the weeds which have emerged above the surface of the soil. For example, the compounds of general formula (I) may be used to control the growth of:

broad-leafed weeds, for example, *Abutlion theophrasti, Amaranthus retroflexus, Bidens pilosa, Chenopodium album, Galium aparine,* Ipomoea spp. e.g. *Ipomoea purpurea, Sesbania exaltata, Sinapis arvensis, Solanum nigrum* and *Xanthium strumarium,* and grass weeds, for example *Alopecurus myosuroides, Arena fatua, Digitaria sanguinalis, Echinochloa crusgalli, Eleusine indica* and Setaria spp, e.g. *Setaria faberii* or *Setaria viridis,* and sedges, for example, *Cyerus esculentus.*

The amounts of compounds of general formula (I) applied vary with the nature of the weeds, the compositions used, the time of application, the climatic and edaphic conditions and (when used to control the growth of weeds in crop-growing areas) the nature of the crops. When applied to a crop-growing area, the rate of application should be sufficient to control the growth of weeds without causing substantial permanent damage to the crop. In general, taking these factors into account, application rates between 0.01 kg and 5 kg of active material per hectare give good results. However, it is to be understood that higher or lower application rates may be used, depending upon the particular problem of weed control encountered.

The compounds of general formula (I) may be used to control selectively the growth of weeds, for example to control the growth of those species hereinbefore mentioned, by pre- or post-emergence application in a directional or non-directional fashion, e.g. by directional or non-directional spraying, to a locus of weed infestation which is an area used, or to be used, for growing crops, for example cereals, e.g. wheat, barley, oats, maize and rice, soya beans, field and dwarf beans, peas, lucerne, cotton, peanuts, flax, onions, carrots, cabbage, oilseed rape, sunflower, sugar beet, and permanent or sown grassland before or after sowing of the crop or before or after emergence of the crop. For the selective control of weeds at a locus of weed infestation which is an area used, or to be used, for growing of crops, e.g. the crops hereinbefore mentioned, application rates between 0.01 kg and 4.0 kg, and preferably between 0.01 kg and 2.0 kg, of active material per hectare are particularly suitable.

The compounds of general formula (I) may also be used to control the growth of weeds, especially those indicated above, by pre- or post-emergence application in established orchards and other tree-growing areas, for example forests, woods and parks, and plantations, e.g. sugar cane, oil palm and rubber plantations. For this purpose they may be applied in a directional or non-directional fashion (e.g. by directional or non-directional spraying) to the weeds or to the soil in which they are expected to appear, before or after planting of the trees or plantations at application rates between 0.25kg and 5.0 kg, and preferably between 0.5 kg and 4.0 kg of active material per hectare.

The compounds of general formula (I) may also be used to control the growth of weeds, especially those indicated above, at loci which are not crop-growing areas but in which the control of weeds is nevertheless desirable.

Examples of such non-crop-growing areas include airfields, industrial sites, railways, roadside verges, the verges of rivers, irrigation and other waterways, scrublands and fallow or uncultivated land, in particular where it is desired to control the growth of weeds in order to reduce fire risks. When used for such purposes in which a total herbicidal effect is frequently desired, the active compounds are normally applied at dosage rates higher than those used in crop-growing areas as hereinbefore described. The precise dosage will depend upon the nature of the vegetation treated and the effect sought.

Pre- or post-emergence application, and preferably pre-emergence application, in a directional or non-directional fashion (e.g. by directional or non-directional spraying) at application rates between 1.0 kg and 20.0 kg, and preferably between 5.0 and 10.0 kg, of active material per hectare are particularly suitable for this purpose.

When used to control the growth of weeds by pre-emergence application, the compounds of general formula (I) may be incorporated into the soil in which the weeds are expected to emerge. It will be appreciated that when the compounds of general formula (I) are used to control the growth of weeds by post-emergence application, i.e. by application to the aerial or exposed portions of emerged weeds, the compounds of general formula (I) will also normally come into contact with the soil and may also then exercise a pre-emergence control on later-germinating weeds in the soil.

Where especially prolonged weed control is required, the application of compounds of general formula (1) may be repeated if required.

According to a further feature of the present invention, there are provided compositions suitable for herbicidal use comprising one or more of the 5-aryl isoxazole derivatives of general formula I, in association with, and preferably homogeneously dispersed in, one or more compatible agriculturally acceptable diluents or carriers and/or surface active agents [i.e. diluents or carriers and/or surface active agents of the type generally accepted in the art as being suitable for use in herbicidal compositions and which are compatible with compounds of general formula (I)]. The term "homogeneously dispersed" is used to include compositions in which the compounds of general formula (I) are dissolved in other components. The term "herbicidal compositions" is used in a broad sense to include not only compositions which are ready for use as herbicides but also concentrates which must be diluted before use. Preferably, the compositions contain from 0.05 to 90% by weight of one or more compounds of general formula (I).

The herbicidal compositions may contain both a diluent or carrier and surface-active (e.g. wetting, dispersing, or emulsifying) agent. Surface-active agents which may be present in herbicidal compositions of the present invention may be of the ionic or non-ionic types, for example sulphoricinoleates, quaternary, ammonium derivatives, products based on condensates of ethylene oxide with alkyl and polyaryl phenols, e.g. nonylo or octyl-phenols, or carboxylic acid esters of anhydrosorbitols which have been rendered soluble by etherification of the free hydroxy groups by condensation with ethylene oxide, alkali and alkaline earth metal salts of sulphuric acid esters and sulphonic acids such as dinonyl- and dioctyl-sodium sulphonosuccinates and alkali and alkaline earth metal salts of high molecular weight sulphonic acid derivatives such as sodium and calcium lignosulphonates and sodium and calcium alkylbenzene sulphonates.

Suitably, the herbicidal compositions according to the present invention may comprise up to 10% by weight, e.g. from 0.05% to 10% by weight, of surface-active agent but, if desired, herbicidal compositions according to the present invention may comprise higher proportions of surface-active agent, for example up to 15% by weight in liquid emulsifiable suspension concentrates and up to 25% by weight in liquid water soluble concentrates.

Examples of suitable solid diluents or carriers are aluminium silicate, talc, calcined magnesia, kieselguhr, tricalcium phosphate, powdered cork, absorbent carbon black and clays such as kaolin and bentonite. The solid compositions (which may take the form of dusts, granules or wettable powders) are preferably prepared by grinding the compounds of general formula (I) with solid diluents or by impregnating the solid diluents or carriers with solutions of the compounds of general formula (I) in volatile solvents, evaporating the solvents and, if necessary, grinding the products so as to obtain powders. Granular formulations may be prepared by absorbing the compounds of general formula (I) (dissolved in suitable solvents, which may, if desired, be volatile) onto the solid diluents or carriers in granular form and, if desired, evaporating the solvents, or by granulating compositions in powder form obtained as described above. Solid herbicidal compositions, particularly wettable powders and granules, may contain wetting or dispersing agents (for example of the types described above), which may also, when solid, serve as diluents or carriers.

Liquid compositions according to the invention may take the form of aqueous, organic or aqueous-organic solutions, suspensions and emulsions which may incorporate a surface-active agent. Suitable liquid diluents for incorporation in the liquid compositions include water, glycols, tetrahydrofurfuryl alcohol, acetophenone, cyclohexanone, isophorone, toluene, xylene, mineral, animal and vegetable oils and light aromatic and naphthenic fractions of petroleum (and mixtures of these diluents). Surface-active agents, which may be present in the liquid compositions, may be ionic or non-ionic (for example of the types described above) and may, when liquid, also serve as diluents or carriers.

Powders, dispersible granules and liquid compositions in the form of concentrates may be diluted with water or other suitable diluents, for example mineral or vegetable oils, particularly in the case of liquid concentrates in which the diluent or carrier is an oil, to give compositions ready for use.

When desired, liquid compositions of the compound of general formula (I) may be used in the form of self-emulsifying concentrates containing the active substances dissolved in the emulsifying agents or in solvents containing emulsifying agents compatible with the active substances, the simple addition of water to such concentrates producing compositions ready for use.

Liquid concentrates in which the diluent or carrier is an oil may be used without further dilution using the electrostatic spray technique.

Herbicidal compositions according to the present invention may also contain, if desired, conventional adjuvants such as adhesives, protective colloids, thickeners, penetrating agents, stabilisers, sequestering agents, anticaking agents, colouring agents and corrosion inhibitors. These adjuvants may also serve as carriers or diluents.

Unless otherwise specified, the following percentages are by weight. Preferred herbicidal compositions according to the present invention are aqueous suspension concentrates which comprise from 10 to 70% of one or more compounds of general formula (I), from 2 to 10% of surface-active agent, from 0.1 to 5% of thickener and from 15 to 87.9% of water; wettable powders which comprise from 10 to 90% of one or more compounds of general formula (I), from 2 to 10% of surface-active agent and from 8 to 88% of solid diluent or carrier;

water soluble or water dispersible powders which comprise from 10 to 90% of one or more compounds of general formula (I), from 2 to 40% of sodium carbonate and from 0 to 88% of solid diluent;

liquid water soluble concentrates which comprise from 5 to 50%, e.g. 10 to 30%, of one or more compounds of general formula (I), from 5 to 25% of surface-active agent and from 25 to 90%, e.g. 45 to 85%, of water miscible solvent, e.g. dimethylformamide, or a mixture of water-miscible solvent and water;

liquid emulsifiable suspension concentrates which comprise from 10 to 70% of one or more compounds of general formula (I), from 5 to 15% of surface-active agent, from 0.1 to 5% of thickener and from 10 to 84.9% of organic solvent;

granules which comprise from 1 to 90%, e.g. 2 to 10% of one or more compounds of general formula (I), from 0.5 to 7%, e.g. 0.5 to 2%, of surface-active agent and from 3 to 98.5%, e.g. 88 to 97.5%, of granular carrier and emulsifiable concentrates which comprise 0.05 to 90%, and preferably from 1 to 60% of one or more compounds of general formula (I), from 0.01 to 10%, and preferably from 1 to 10%, of surface-active agent and from 9.99 to 99.94 %, and preferably from 39 to 98.99%, of organic solvent.

Herbicidal compositions according to the present invention may also comprise the compounds of general formula (I) in association with, and preferably homogeneously dispersed in, one or more other pesticidally active compounds and, if desired, one or more compatible pesticidally acceptable diluents or carriers, surface-active agents and conventional adjuvants as hereinbefore described. Examples of other pesticidally active compounds which may be included in, or used in conjunction with, the herbicidal compositions of the present invention include herbicides, for example to increase the range of weed species controlled for example alachlor [2-chloro-2,6'-diethyl-N-( methoxy-methyl )-acetanilide], atrazine [2-chloro-4-ethylamino-6-isopropylamino-1,3,5-triazine], bromoxynil [3,5-dibromo-4hydroxybenzonitrile], chlortoluron [N'-(3-chloro-4-methylphenyl)-N,N-dimethylurea]cyanazine[2-chloro-4-( 1-cyano- 1- methylethylamino)-6 -ethylamino- 1,3,5-triazine], 2,4-D [2,4-dichlorophenoxy-acetic acid], dicamba [3,6-dichloro-2-methoxybenzoic acid], difenzoquat [1,2- dimethyl-3,5-diphenylpyrazolium salts], flampropmethyl [methyl N-2-(N-benzoyl-3-chloro4-fluoroanilino)-propionate], fluometuron [N'-(3-trifluoro- methylphenyl)-N,N-dimethylurea], isoproturon [N'-(4-isopropylphenyl)-N,N-dimethylurea], insecticides, e.g. synthetic pyrethroids, e.g. permethrin and cypermethrin, and fungicides, e.g. carbamates, e.g. methyl N-( 1-butyl-carbamoyl- benzimidazol-2yl)carbamate, and triazoles e.g. 1-(4-chloro-phenoxy)-3,3-dimethyl-l-(1,2,4-triazol-1-yl )-butan-2-one.

Pesticidally active compounds and other biologically active materials which may be included in, or used in conjunction with, the herbicidal compositions of the present invention, for example those hereinbefore mentioned, and which are acids, may, if desired, be utilized in the form of conventional derivatives, for example alkali metal and amine salts and esters.

According to a further feature of the present invention there is provided an article of manufacture comprising at least one of the 5-aryl isoxazole derivatives of general formula (I) or, as is preferred, a herbicidal composition as hereinbefore described, and preferably a herbicidal concentrate which must be diluted before use, comprising at least one of the 5-aryl isoxazole derivatives of general formula (I) within a container for the aforesaid derivative or derivatives of general formula (I), or a said herbicidal composition, and instructions physically associated with the aforesaid container setting out the manner in which the aforesaid derivative or derivatives of general formula (I) or herbicidal composition contained therein is to be used to control the growth of weeds. The containers will normally be of the types conventionally used for the storage of chemical substances which are solid at normal ambient temperatures and herbicidal compositions particularly in the form of concentrates, for example cans and drums of metal, which may be internally lacquered, and plastics materials, bottles or glass and plastics materials and, when the contents of the container is a solid, for example granular, herbicidal compositions, boxes, for example of cardboard, plastics materials and metal, or sacks. The containers will normally be of sufficient capacity to contain amounts of the 5-aryl isoxazole derivative or herbicidal compositions sufficient to treat at least one acre of ground to control the growth of weeds therein but will not exceed a size which is convenient for conventional methods of handling. The instructions will be physically associated with the container, for example by being printed directly thereon or on a label or tag affixed thereto. The directions will normally indicate that the contents of the container, after dilution if necessary, are to be applied to control the growth of weeds at rates of application between 0.01 kg and 20 kg of active material per hectare in the manner and for the purposes hereinbefore described.

The following Examples illustrate herbicidal compositions according to the present invention:

EXAMPLE C1

A soluble concentrate is formed from:

| | |
|---|---|
| Active ingredient (compound 1) | 29% w/v |
| Potassium hydroxide solution 33% w/v | 10% v/v |
| Tetrahydrofurfuryl alcohol (THFA) | 10% v/v |
| Water | to 100 volumes. | by stirring THFA, active ingredient (compound1) and 90% volume of water and slowly adding the potassium hydroxide solution until a steady pH 7-8 is obtained then making up to volume with water.

Similar soluble concentrates may be prepared as described above by replacing the isoxazole (compound 1) with other compounds of general formula (I).

EXAMPLE C2

A wettable powder is formed from:

| | |
|---|---|
| Active ingredient (compound 1) | 50% w/w |
| Sodium dodecylbenzene sulphonate | 3% w/w |
| Sodium lignosulphate | 5% w/w |
| Sodium formaldehyde alkylnaphthalene sulphonate | 2% w/w |
| Microfine silicon dioxide | 3% w/w and |
| China clay | 37% w/w | by blending the above ingredients together and grinding the mixture in an air jet mill.

Similar wettable powders may be prepared as described above by replacing the isoxazole (compound 1) with other compounds of general formula (I).

EXAMPLE C3

A water soluble powder is formed from:

| | |
|---|---|
| Active ingredient (compound 1) | 50% w/w |
| Sodium dodecylbenzenesulphonate | 1% w/w |
| Microfine silicon dioxide | 2% w/w |
| Sodium bicarbonate | 47% w/w | by mixing the above ingredients and grinding the above mixture in a hammer mill.

Similar water soluble powders may be prepared as described above by replacing the isoxazole (compound 1) with other compounds of general formula (I).

Representative compounds of the invention have been used in herbicidal applications according to the following procedures.

METHOD OF USE OF HERBICIDAL COMPOUNDS:

a) General

Appropriate quantities of the compounds used to treat the plants were dissolved in acetone to give solutions equivalent to application rates of up to 4000 g test compound per hectare (g/ha). These solutions were applied from a standard laboratory herbicide sprayer delivering the equivalent of 290 liters of spray fluid per hectare.

b) Weed Control: pre-emergence

The seeds were sown in 70 mm square, 75 mm deep plastic pots in non-sterile soil. The quantities of seed per pot were as follows:

| Weed species | Approx number of seeds/pot |
|---|---|
| 1) Broad-leafed weeds | |
| Abutilon theophrasti | 10 |
| Amaranthus retroflexus | 20 |
| Galium aparine | 10 |
| Ipomoea purpurea | 10 |
| Sinapis arvensis | 15 |
| Xanthium strumarium | 2. |
| 2) Grass weeds | |
| Alopecurus myosuroides | 15 |
| Avena fatua | 10 |
| Echinochloa crus-galli | 15 |
| Setaria viridis | 20. |
| 3) Sedges | |
| Cyperus esculentus | 3. |
| Crop | |
| 1) Broad-leafed | |
| Cotton | 3 |
| Soya | 3. |
| 2) Grass | |
| Maize | 2 |
| Rice | 6 |
| Wheat | 6. |

The compound of the invention was applied to the soil surface, containing the seeds, as described in (a). A single pot of each crop and each weed was allocated to each treatment, with unsprayed controls and controls sprayed with acetone alone.

After treatment the pots were placed on capillary matting kept in a glass house, and watered overhead. Visual assessment of crop damage was made 20–24 days after spraying. The results were expressed as the percentage reduction in growth or damage to the crop or weeds, in comparison with the plants in the control pots.

c) Weed control: Post-emergence

The weeds and crops were sown directly into John Innes potting compost in 75 mm deep, 70 mm square pots except for Amaranthus which was pricked out at the seedling stage and transferred to the pots one week before spraying. The plants were then grown in the greenhouse until ready for spraying with the compounds used to treat the plants. The number of plants per pot were as follows:

|  | Number of plants per pot | Growth stage |
| --- | --- | --- |
| Weed species |  |  |
| 1) Broad leafed weeds |  |  |
| Abutilon theophrasti | 3 | 1-2 leaves |
| Amaranthus retroflexus | 4 | 1-2 leaves |
| Galium aparine | 3 | 1st whorl |
| Ipomoea purpurea | 3 | 1-2 leaves |
| Sinapis arvensis | 4 | 2 leaves |
| Xanthium strumarium | 1 | 2-3 leaves. |
| 2) Grass weeds |  |  |
| Alopecurus myosuroides | 8-12 | 1-2 leaves |
| Avena fatua | 12-18 | 1-2 leaves |
| Echinochloa crus-galli | 4 | 2-3 leaves |
| Setaria viridis | 15-25 | 1-2 leaves. |
| 3) Sedges |  |  |
| Cyperus esculentus | 3 | 3 leaves. |
| Crops |  |  |
| 1) Broad leafed |  |  |
| Cotton | 2 | 1 leaf |
| Soya | 2 | 2 leaves. |
| 2) Grass |  |  |
| Maize | 2 | 2-3 leaves |
| Rice | 4 | 2-3 leaves |
| Wheat | 5 | 2-3 leaves. |

The compound used to treat the plants was applied to the plants as described in (a). A single pot of each crop and weed species was allocated to each treatment, with unsprayed controls and controls sprayed with acetone alone.

After treatment the pots were placed on capillary matting in a glass house, and watered overhead once after 24 hours and then by controlled sub-irrigation. Visual assessment of crop damage and weed control was made 20-24 days after spraying. The results were expressed as the percentage reduction in growth or damage to the crop or weeds, in comparison with the plants in the control pots.

The compounds of the invention, used at 4 kg/ha or less, have shown an excellent level of herbicidal activity, together with crop tolerance on the weeds used in the foregoing experiments.

When applied pre-emergence at 1000 g/ha compounds 1 to 13 gave at least 90% reduction in growth of one or more of the weed species, with selectivity: in at least one crop species.

When applied post-emergence at 1000 g/ha compounds 1 to 13 gave at least 90% reduction in growth of one or more of the weed species, with selectivity in at least one crop species.

While the invention has been described in terms of various preferred embodiments, the skilled artisan will appreciate that various modifications, substitutions, omissions and changes may be made without departing from the spirit thereof. Accordingly, it is intended that the scope of the present invention be limited solely by the scope of the following claims, including equivalents thereof.

What is claimed is:

1. A compound of the formula

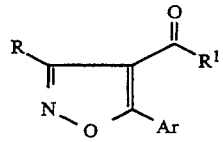

wherein:
Ar represents a phenyl radical substituted by from one to five $R^2$ groups;
R represents:
hydrogen, $-CO_2R^3$, $-COR^4$, cyano, halogen, or a straight- or branched-chain alkyl radical having up to 4 carbon atoms which is optionally substituted by one or more halogen atoms;
$R^1$ represents:
a straight- or branched-chain alkyl radical having up to 6 carbon atoms which is optionally substituted by one or more halogen atoms or by a cycloalkyl radical having from 3 to 6 carbon atoms; or
a cycloalkyl radical having from 3 to 6 carbon atoms optionally substituted by one or more $R^4$ groups or one or more halogen atoms;
each $R^2$ is independently selected from the group consisting of:
a halogen atom, $R^4$, nitro, $-CO_2R^3$, $-OR^4$, $-S(O)_mR^4$, $-S(O)_mR^5$, $-O-(CH_2)_p-OR^4$, and a straight- or branched-chain alkyl radical having up to 6 carbon atoms which is substituted by $-OR^4$;
$R^3$ and $R^4$, which may be the same or different, each represent:
a straight- or branched-chain alkyl radical having up to 6 carbon atoms which is optionally substituted by one or more halogen atoms;
$R^5$ represents a phenyl radical optionally substituted by from one to five groups selected from halogen, nitro, $R^4$ and $-OR^4$;
p represents an integer from 1 to 3; and
m represents zero, 1 or 2;
with the provisos that:
(a) when R represents hydrogen, $R^1$ is:
(1) a straight- or branched-chain alkyl radical having up to 6 carbon atoms substituted by a cycloalkyl radical having from 3 to 6 carbon atoms; or
(2) a cycloalkyl radical having from 3 to 6 carbon atoms optionally substituted by one or more $R^4$ groups or one or more halogen atoms; and
(b) when R and $R^1$ both represent methyl, Ar is not 2,3,4,5,6-pentamethylphenyl.

2. The compound according to claim 1, wherein R represents hydrogen.

3. The compound according to claim 1, wherein R represents $-CO_2R^3$ wherein $R^3$ is as defined in claim 1.

4. The compound according to claim 1, wherein R represents $-COR^4$ wherein $R^4$ is as defined in claim 1.

5. The compound according to claim 1, wherein R represents cyano.

6. The compound according to claim 1, wherein R represents halogen.

7. The compound according to claim 1, wherein R represents a straight- or branched-chain alkyl radical having up to 4 carbon atoms which is optionally substituted by one or more halogen atoms.

8. The compound according to claim 1, wherein $R^1$ represents a straight- or branched-chain alkyl radical having up to 6 carbon atoms which is optionally substituted by one or more halogen atoms or by a cycloalkyl radical having from 3 to 6 carbon atoms.

9. The compound according to claim 1, wherein $R^1$ represents a cycloalkyl radical having from 3 to 6 carbon atoms optionally substituted by one or more halogen atoms or one or more $R^4$ groups wherein $R^4$ is as defined in claim 1.

10. The compound according to claim 1, wherein at least one $R^2$ group is a halogen atom.

11. The compound according to claim 1, wherein at least one $R^2$ group is $R^4$, wherein $R^4$ is as defined in claim 1.

12. The compound according to claim 1, wherein at least one $R^2$ is nitro.

13. The compound according to claim 1, wherein at least one $R^2$ is $-CO_2R^3$ wherein $R^3$ is as defined in claim 1.

14. The compound according to claim 1, wherein at least one $R^2$ is $-OR^4$ wherein $R^4$ is as defined in claim 1.

15. The compound according to claim 1, wherein at least one $R^2$ is $-S(O)_mR^4$ wherein $R^4$ and m are as defined in claim 1.

16. The compound according to claim 1, wherein at least one $R^2$ is $-S(O)_mR^5$ wherein $R^5$ and m are as defined in claim 1.

17. The compound according to claim 1, wherein at least one $R^2$ is $-O-(CH_2)_p-OR^4$ wherein $R^4$ and p are as defined in claim 1.

18. The compound according to claim 1, wherein at least one $R^2$ is a straight- or branched-chain alkyl radical having up to 6 carbon atoms which is substituted by $-OR^4$, wherein $R^4$ is as defined in claim 1.

19. The compound according to claim 1, wherein Ar represents a phenyl radical substituted by one $R^2$ group.

20. The compound according to claim 19, wherein $R^2$ is $-S(O)_mCH_3$ wherein m is zero, 1 or 2.

21. The compound according to claim 1, wherein Ar represents a phenyl radical substituted by two $R^2$ groups.

22. The compound according to claim 21, wherein both $R^2$ groups are halogen.

23. The compound according to claim 21, wherein one $R^2$ group is halogen and the other $R^2$ group is $-S(O)_mCH_3$ wherein m is zero, 1 or 2.

24. The compound according to claim 21, wherein one $R^2$ groups is trifluoromethyl and the other $R^2$ group is $-S(O)_mCH_3$ wherein m is zero, 1 or 2.

25. The compound according to claim 21, wherein one $R^2$ group is trifluoromethyl and the other $R^2$ group is

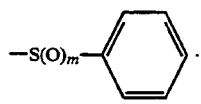

26. The compound according to claim 1, wherein Ar represents a phenyl radical substituted by from one to five $R^2$ groups and each $R^2$ is independently selected from the group consisting of a halogen atom, $R^4$, nitro, $-CO_2R^3$, $-OR^4$, $-S(O)_mR^4$, $-O-(CH_2)_p-OR^4$ and a straight- or branched-chain alkyl group having up to 6 carbons which is substituted by $-OR^4$, wherein $R^3$ and $R^4$ are as defined in claim 1.

27. The compound according to claim 1, wherein R is selected from the group consisting of hydrogen, $-CO_2R^3$ and $-COR^4$, wherein $R^3$ and $R^4$ are as defined in claim 1, and Ar represents a phenyl radical substituted by from one to three $R^2$ groups wherein $R^2$ is as defined in claim 1.

28. The compound according to claim 26, wherein R is selected from the group consisting of hydrogen, $-CO_2R^3$ and $-COR^4$, wherein $R^3$ and $R^4$ are as defined in claim 26, and Ar represents a phenyl radical substituted by from one to three $R^2$ groups wherein $R^2$ is as defined in claim 26.

29. The compound according to claim 1, wherein Ar represents a phenyl radical substituted by one or two $R^2$ groups; R represents hydrogen or $-CO_2R^3$ wherein $R^3$ is as defined in claim 1; $R^1$ represents cyclopropyl; and each $R^2$ is independently selected from the group consisting of halogen, $R^4$, $-S(O)_mR^4$ and $-S(O)_mR^5$, wherein $R^4$, $R^5$ and m are as defined in claim 1.

30. The compound which is:
4-cyclopropylcarbonyl-5-(2-fluoro-4-methylsulphonylphenyl)isoxazole;
4-cyclopropylcarbonyl-5-(3,4-dichlorophenyl)isoxazole;
4-cyclopropylcarbonyl-5-[4-(methylsulphenyl)phenyl]isoxazole;
4-cyclopropylcarbonyl-5-[3-chloro-4-(methylsulphenyl)phenyl]isoxazole;
4-cyclopropylcarbonyl-5-[3-chloro-4-(methylsulphonyl)phenyl]isoxazole;
4-cyclopropylcarbonyl-5-[4-(methylsulphonyl)phenyl]isoxazole;
4-cyclopropylcarbonyl-5-[4-(methylsulphinyl)phenyl]isoxazole;
4-cyclopropylcarbonyl-5-[3-(methylsulphenyl)phenyl]isoxazole;
ethyl 5-[2-chloro-4-(methylsulphenyl)phenyl]-4-cyclopropylcarbonylisoxazole-3-carboxylate;
ethyl 4-cyclopropylcarbonyl-5-[2-(methylsulphenyl)-4-trifluoromethylphenyl]isoxazole-3-carboxylate;
1-methylethyl 4-cyclopropylcarbonyl-5-[2-(methylsulphenyl)-4-trifluoromethylphenyl]isoxazole-3-carboxylate; or
4-cyclopropylcarbonyl-5-[2-(phenylsulphenyl)-4-trifluoromethylphenyl]isoxazole;

31. A herbicidal composition comprising a herbicidally effective amount of a compound of the formula

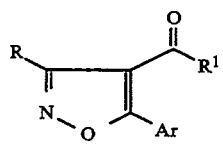

wherein:
Ar represents a phenyl radical substituted by from one to five $R^2$ groups;
R represents:
hydrogen, $-CO_2R^3$, $-COR^4$, cyano, halogen, or a straight- or branched-chain alkyl radical having up to 4 carbon atoms which is optionally substituted by one or more halogen atoms;
$R^1$ represents:
a straight- or branched-chain alkyl radical having up to 6 carbon atoms which is optionally substituted by one or more halogen atoms or by a cycloalkyl radical having from 3 to 6 carbon atoms; or a cycloalkyl radical having from 3 to 6 carbon atoms optionally substituted by one or more $R^4$ groups or one or more halogen atoms;

each $R^2$ is independently selected from the group consisting of:

a halogen atom, $R^4$, nitro, $-CO_2R^3$, $-OR^4$, $-S(O)_mR^4$, $-S(O)_mR^5$, $-O-(CH_2)_p-OR^4$, and a straight- or branched-chain alkyl radical having up to 6 carbon atoms which is substituted by $-OR^4$;

$R^3$ and $R^4$, which may be the same or different, each represent:

a straight- or branched-chain alkyl radical having up to 6 carbon atoms which is optionally substituted by one or more halogen atoms;

$R^5$ represents a phenyl radical optionally substituted by from one to five groups selected from halogen, nitro, $R^4$ and $-OR^4$;

p represents an integer from 1 to 3; and m represents zero, 1 or 2; and an agriculturally acceptable surface-active agent.

32. A herbicidal composition comprising a herbicidally effective amount of a compound of formula (I) as defined in claim 1 and at least one member selected from the group consisting of agriculturally acceptable diluents and surface-active agents.

33. The herbicidal composition according to claim 31, comprising from about 0.05 to about 90% by weight of compound of formula (I).

34. The herbicidal composition according to claim 32, comprising from about 0.05 to about 90% by weight of compound of formula (I).

35. The herbicidal composition according to claim 31, which is in liquid form and comprises from about 0.05 to about 25% of surface-active agent.

36. The herbicidal composition according to claim 32, which is in liquid form and comprises from about 0.05 to about 25% of surface-active agent.

37. The herbicidal composition according to claim 33, which is in liquid form and comprises from about 0.05 to about 25% of surface-active agent.

38. The herbicidal composition according to claim 34, which is in liquid form and comprises from about 0.05 to about 25% of surface-active agent.

39. The herbicidal composition according to claim 31, which is in the form of an aqueous suspension concentrate, a wettable powder, a water soluble or water dispersible powder, a liquid water soluble concentrate, a liquid emulsifiable suspension concentrate, a granule or an emulsifiable concentrate.

40. A method for controlling the growth of weeds at a locus comprising applying to said locus a herbicidally effective amount of a compound of the formula

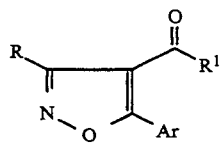

wherein:

Ar represents a phenyl radical substituted by from one to five $R^2$ groups;

R represents:

hydrogen, $-CO_2R^3$, $-COR^4$, cyano, halogen, or a straight- or branched-chain alkyl radical having up to 4 carbon atoms which is optionally substituted by one or more halogen atoms;

$R^1$ represents:

a straight- or branched-chain alkyl radical having up to 6 carbon atoms which is optionally substituted by one or more halogen atoms or by a cycloalkyl radical having from 3 to 6 carbon atoms; or a cycloalkyl radical having from 3 to 6 carbon atoms optionally substituted by one or more $R^4$ groups or one or more halogen atoms;

each $R^2$ is independently selected from the group consisting of:

a halogen atom, $R^4$, nitro, $-CO_2R^3$, $-OR^4$, $-S(O)_mR^4$, $-S(O)_mR^5$, $-O-(CH_2)_p-OR^4$, and a straight- or branched-chain alkyl radical having up to 6 carbon atoms which is substituted by $-OR^4$;

$R^3$ and $R^4$, which may be the same or different, each represent:

a straight- or branched-chain alkyl radical having up to 6 carbon atoms which is optionally substituted by one or more halogen atoms;

$R^5$ represents a phenyl radical optionally substituted by from one to five groups selected from halogen, nitro, $R^4$ and $-OR^4$;

p represents an integer from 1 to 3; and m represents zero, 1 or 2.

41. A method for controlling the growth of weeds at a locus comprising applying to said locus a herbicidally effective amount of a compound of formula (I) as defined in claim 1.

42. The method according to claim 40, wherein said locus is an area used, or to be used, for growing crops and the compound of formula (I) is applied at an application rate of from about 0.01 kg to about 4.0 kg per hectare.

43. The method according to claim 41, wherein said locus is an area used, or to be used, for growing crops and the compound of formula (I) is applied at an application rate of from about 0.01 kg to about 4.0 kg per hectare.

44. The method according to claim 40, wherein said locus is not a crop-growing area and the compound of formula (I) is applied at an application rate of from about 1.0 to about 20.0 kg per hectare.

45. The method according to claim 41, wherein said locus is not a crop-growing area and the compound of formula (I) is applied at an application rate of from about 1.0 to about 20.0 kg per hectare.

* * * * *